US00PP11638P

United States Patent [19]

Olesen et al.

[11] Patent Number: Plant 11,638

[45] Date of Patent: Nov. 21, 2000

[54] COMPACT FLORIBUNDA ROSE PLANT NAMED 'POULSIANA'

[75] Inventors: L. Pernille Olesen; Mogens N. Olesen, both of Fredensborg, Denmark

[73] Assignee: Poulsen Roser ApS, Fredensborg, Denmark

[21] Appl. No.: 09/165,412

[22] Filed: Oct. 2, 1998

[51] Int. Cl.[7] ..... A01H 5/00

[52] U.S. Cl. ..... Plt./145

[58] Field of Search ..... Plt./145, 118, 125

*Primary Examiner*—Howard J. Locker

[57] ABSTRACT

A new compact floribunda rose plant which has abundant, yellow flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

The present invention constitutes a new and distinct variety of compact floribunda rose plant which originated from a controlled crossing between an unnamed seedling and 'POULsun' (U.S. Plant Pat. No. 9,716). The two parents were crossed and the resulting seeds were planted in a controlled environment. The new variety is named 'POULsiana'.

The new rose may be distinguished from its seed parent, an unnamed seedling by the same inventors, by the following combination of characteristics:

1. 'POULsiana' is a bright yellow, compact floribunda and the seed parent is a yellow miniature.

2. The unnamed seedling resulted from a crossing of RUImired, U.S. Plant Pat. No. 5,770 and a yellow patio rose.

3. The flowers of the unnamed seedling are smaller and the plant growth is more compact than 'POULsiana'.

The new variety may be distinguished from its pollen parent, 'POULsun' created by the same inventors, by the following combination of characteristics:

1. The flower color of 'POULsiana' is a brighter yellow than the flowers of 'POULsun'.

2. 'POULsun' has more double flowers and is shorter than 'POULsiana'.

3. 'POULsun' has more fragrance than 'POULsiana'.

The objective of the hybridization of this rose variety for commercial greenhouse culture was to create a new and distinct variety with unique qualities, such as:

1. Uniform and abundant flowers;

2. Vigorous and compact growth;

3. Year-round flowering under glasshouse conditions;

4. Suitability for production from softwood cuttings in pots;

5. Durable flowers and foliage which make a variety suitable for distribution in the floral industry.

This combination of qualities is not present in previously available commercial cultivars of this type and distinguish 'POULsiana' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULsiana' was selected by the inventors as a single plant from the progeny of the hybridization in March, 1993.

Asexual reproduction of 'POULsiana' by cuttings and traditional budding was first done by L. Pernille and Mogens N. Olesen in their nursery in Fredensborg, Denmark in April, 1996. This initial and other subsequent propagations conducted in controlled environments have demonstrated that the characteristics of 'POULsiana' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULsiana'. Specifically illustrated in sheet 1:

1. Stem showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a detailed description of 'POULsiana', as observed in its growth in glasshouses in Fredensborg, Denmark and Burlington, Canada; and in a field nursery in Jackson County, OR. Color references are made using The Royal Horticultural Society (London, England) Colour Chart, 1995, except where common terms of color are used.

For a comparison, several physical characteristics of the rose variety 'POULsun', a patented rose variety from the same inventors described and illustrated in U.S. Plant Pat. No. 9,716 and issued on Dec. 3, 1996 are compared to 'POULsiana' in Chart 1.

CHART 1

| | 'POULsiana' | 'POULsun' |
|---|---|---|
| Petal count | 15–20 | 30–35 |
| Upper petal surface, open bloom | Yellow Group 7B | Yellow Group 13A |

-continued

CHART 1

| | 'POULsiana' | 'POULsun' |
|---|---|---|
| Size of plant in a pot | 22–24 cm (h) × 20–22 cm (w) | 18–20 cm (h) × 18–20 cm (w) |

Parents: Unnamed seedling×'POULsun'.
Classification:
*Botanical.*—*Rosa hybrida.*
*Commercial.*—Compact floribunda.

FLOWER AND FLOWER BUD

Blooming habit: Recurrent.
Flower bud:
*Size.*—Upon opening, 23 mm–25 mm in length from base of receptacle to flower tip.
*Bud form.*—Ovoid to globular.
*Bud color.*—As sepals unfold, Yellow Group 7B. Yellow Group 7B at ¼ opening. On plants grown under high light conditions, some guard petals exhibit red intonations, Red Group 44C.
*Sepals.*—Green Group 138A. Base of outside of sepal is Green Group 138B lighter in color. Some sepals with intonations of Greyed-Red Group 179A. Weak foliaceous appendages on three of the five sepals. Surfaces of sepals lightly pubescent.
*Stipitate glands.*—Exterior surfaces of all 5 sepals with moderate number of stipitate glands.
*Peduncle.*—Surface: With a moderate number of stipitate glands. Length: 25–35 mm average length. Color: Between Yellow-Green Group 143B–143C. On plants grown under high light conditions, penduncles may exhibit intonations of Greyed-Red Group 184A. Strength: Upright.
*Receptacle.*—Surface: Slightly pubescent. Shape: Broadly funnel- shaped. Size: Medium. 6 mm×6 mm. Color: Green Group 143C.
*Borne.*—Singly and in small clusters.
Flower bloom:
*Size.*—Average diameter is 55 mm–60 mm when open.
*Form.*—Shape of flower when viewed from the side: Upon opening, upper part: Flattened convex. Upon opening, lower part: Flattened convex. Open flower, upper part: Flattened convex. Open flower, lower part: Flat.
*Petalage.*—Semi-double. Average range: 15–20 under normal conditions.
Color:
*Upon opening, petals.*—Upper Surface: Yellow Group 7A. Reverse Side: Yellow Group 7B.
*After opening, petals.*—Upper Surface: Yellow Group 7B. Reverse Side: Yellow Group 7C.
*Upon opening, basal petal spot.*—No distinctive coloration at petal base observed.
General Tonality: No change in the general tonality at the end of the third day. At the end of 4 to 5 days, general tonality is Yellow Group 7C.
Petals:
*Petal reflex.*—Petals reflex backwards only slightly after bloom opens.
*Petal edge.*—Point in center. Some undulation.
*Petaloids.*—Commonly none.
*Fragrance.*—Light resinous fragrance.
*Duration.*—As a pot plant, flowers last from 8 to 10 days. As a cut flower 5 to 6 days. Petals drop cleanly away from spent blooms.
*Texture.*—Average.
*Shape.*—Round.
*Form.*—Reflexed slightly.
*Arrangement.*—Regular.
Reproductive organs: Reproductive organs visible on open flowers.
*Pollen.*—Color: Greyed-Orange Group 167A. Abundance: Above average.
*Anthers.*—Arrangement: Regular. Size: Small. Color: Yellow-Orange Group 22A. Abundance: Above average.
*Filaments.*—Color: Yellow-Green Group 154B.
*Stigmas.*—Generally at same level with some stigmas superior in location to anthers. Color: Green-Yellow Group 1C.
*Styles.*—Color: Green-White Group 157B.
*Hips.*—None observed.

PLANT

Plant growth: Vigorous, compact, upright to bushy. When grown as a 15 cm pot plant, the average height of the plant itself is 22 to 24 cm and the average width is 22 cm.
Stems:
*Color.*—Young wood: Yellow-Green Group 144A. On plants grown under high light conditions, younger stems may exhibit intonations of Greyed-Red Group 179A. Older wood: Yellow-Green Group 144A.
*Prickles.*—Incidence: Average. Size: Average length: 4 mm. Color: Yellow-Green Group 145C. On plants grown under high light conditions, with red intonations of Greyed-Red Group 179A. Shape: Linear to downward hooked.
*Bark.*—Young wood: Smooth. Older wood: Smooth.
Plant foliage: Normal number of leaflets on normal leaves in middle of the stem: 5–7 leaflets.
*Leaf size.*—Medium. 85–90 mm (1)×60 mm (w).
*Abundance.*—Above average.
*Color.*—Upper Leaf Surface: Green Group 137A–138A. Lower Leaf Surface: Green Group 138B–138C. Juvenile foliage: Green Group 143B. On plants grown under high light conditions, rachis, leaflet margins, petioles and stipules may exhibit intonations of Greyed-Red Group 179A.
Plant leaves and leaflets:
*Stipules.*—Present. Limited hairs on edges of stipules. Size: 8 mm–12 mm. Color: Green Group 138A.
*Petiole.*—Length: 15 mm–17 mm. Color: Green Group 138A. Margins: With stipitate glands.
*Rachis.*—Color: Green Group 138A, Intonations on upper surface of Greyed- Orange Group 173A. Prickles: Present. Similar to on stem. Linear.
*Leaflet.*—Edge: Serrated. Shape: Ovate.
*Other.*—Moderately glossy. Average thickness.
Disease resistance: Above average resistance to mildew and Botrytis under normal growing conditions in Fredensborg, Denmark and Jackson County, OR.
We claim:
1. A new and distinct variety of rose plant of the compact floribunda class, substantially as herein illustrated and described as a distinct and novel rose variety due to its abundant, yellow flowers, vigorous and compact growth, year round flowering under glasshouse conditions, suitability for production from softwood cuttings in pots, and durable flowers and foliage which make the variety suitable for distribution in the floral industry.

* * * * *

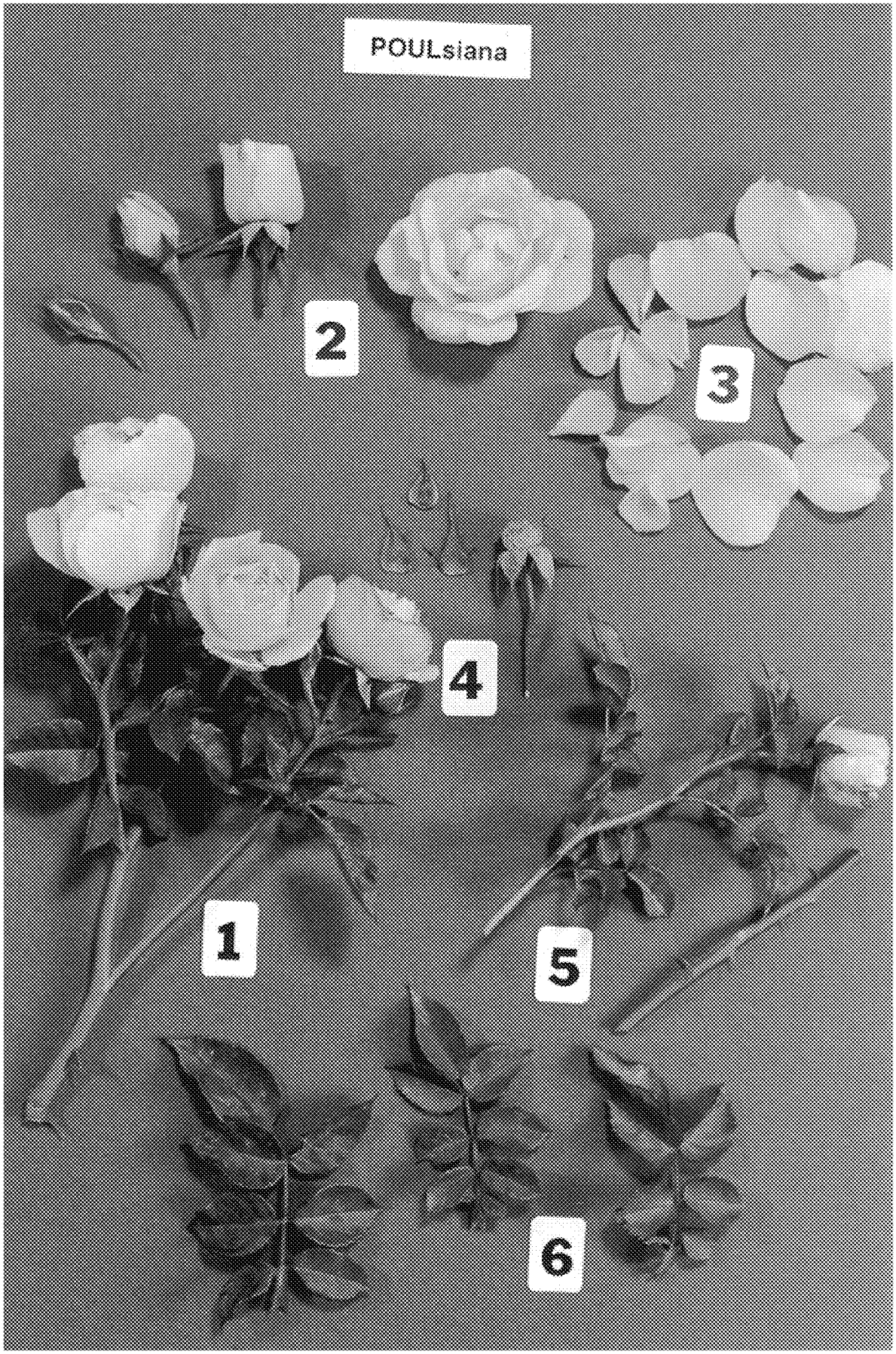
POULsiana
2
3
4
1
5
6